United States Patent [19]

Schiller

[11] Patent Number: 4,544,267

[45] Date of Patent: Oct. 1, 1985

[54] FINGER IDENTIFICATION

[75] Inventor: Michael Schiller, Riverside, N.Y.

[73] Assignee: Fingermatrix, Inc., North White Plains, N.Y.

[21] Appl. No.: 472,640

[22] Filed: Mar. 7, 1983

Related U.S. Application Data

[63] Continuation-in-part of Ser. No. 210,174, Nov. 25, 1980, abandoned, which is a continuation-in-part of Ser. No. 42,605, May 25, 1979, abandoned, which is a continuation-in-part of Ser. No. 844,719, Oct. 25, 1977, abandoned, which is a continuation-in-part of Ser. No. 891,497, Mar. 20, 1978, abandoned, which is a continuation-in-part of Ser. No. 844,580, Oct. 25, 1977, abandoned, which is a continuation-in-part of Ser. No. 396,813, Jul. 9, 1982, abandoned.

[51] Int. Cl.[4] .............................................. G06K 9/20
[52] U.S. Cl. ...................................................... 356/71
[58] Field of Search ........................... 356/71; 382/4-5

[56] References Cited

U.S. PATENT DOCUMENTS

| | | | |
|---|---|---|---|
| 3,138,059 | 6/1964 | White | 356/71 |
| 3,174,414 | 3/1965 | Myer | 356/71 |
| 3,443,098 | 5/1969 | Lewis | 356/71 |
| 3,614,737 | 10/1971 | Sadowsky | 356/71 |
| 3,619,060 | 11/1971 | Johnson | 356/71 |
| 3,743,421 | 7/1973 | Maloney | 356/71 |
| 4,003,656 | 1/1977 | Leventhal | 356/71 |
| 4,053,228 | 10/1977 | Schiller | 356/71 |
| 4,210,899 | 7/1980 | Swonger et al. | 356/71 |
| 4,322,163 | 3/1982 | Schiller | 356/71 |

Primary Examiner—William H. Punter
Attorney, Agent, or Firm—McAulay, Fields, Fisher, Goldstein & Nissen

[57] ABSTRACT

A finger pressed against a platen or a fingerprint card provides a fingerprint object which is scanned by an interrogating beam of collimated light that is linearly displaced across the platen thereby maintaining a constant angle between the interrogating light beam and the plane of the object being scanned. As the beam scans across the fingerprint object, the reflected light beam is modulated. The modulated beam is imaged onto a linear array of photo-responsive devices to provide a series of output signals indicative of modulation information. The outputs of the devices are serially interrogated at each of successive scan positions to provide a set of signals containing fingerprint information.

13 Claims, 14 Drawing Figures

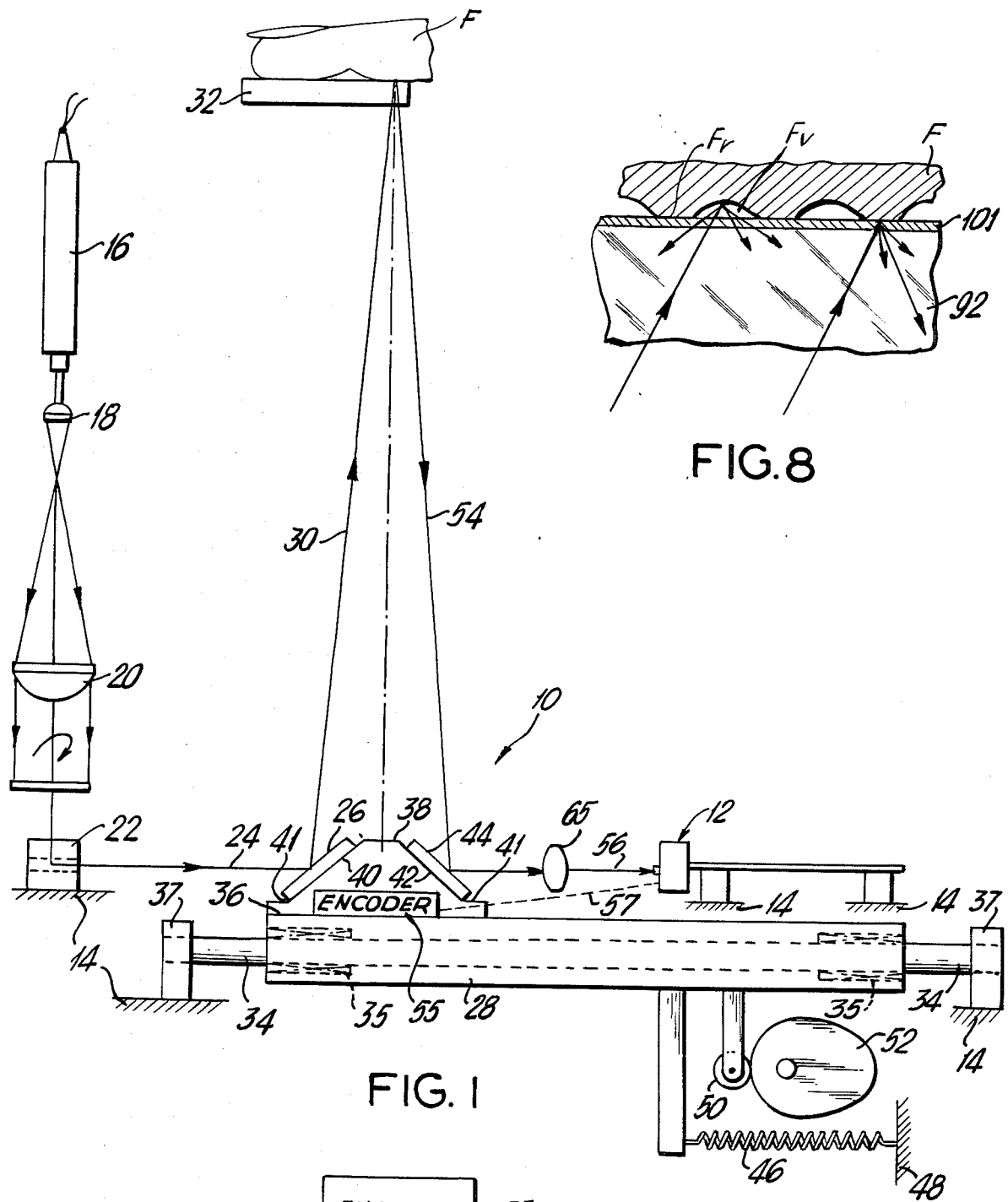
FIG. 8
FIG. 1
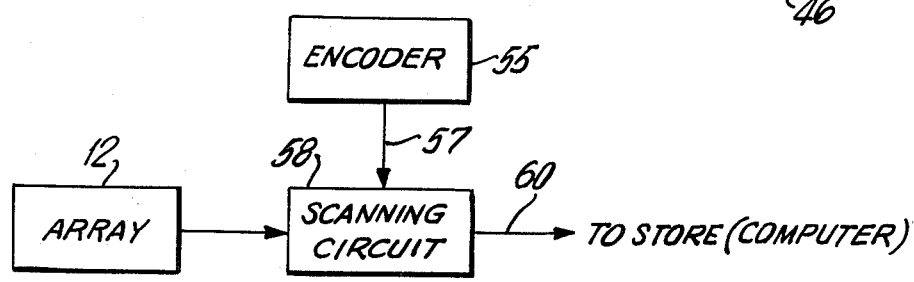
FIG. 2

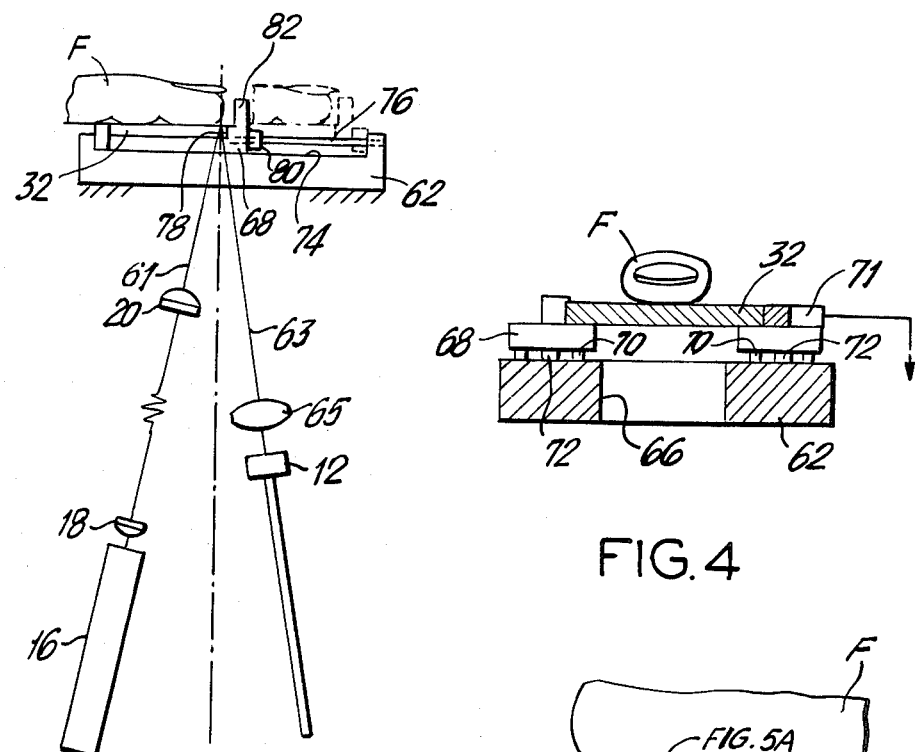
FIG. 3
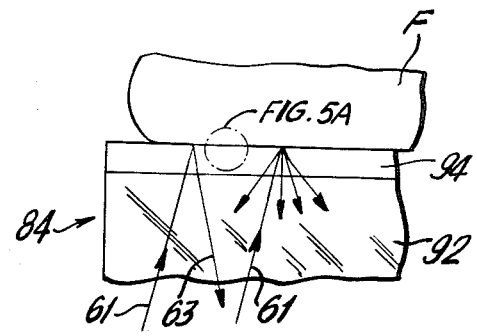
FIG. 4
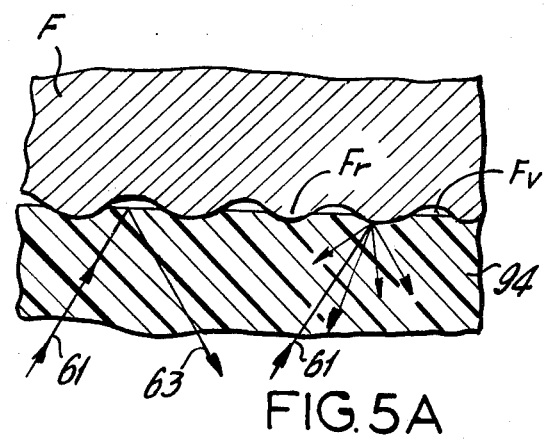
FIG. 5
FIG. 5A
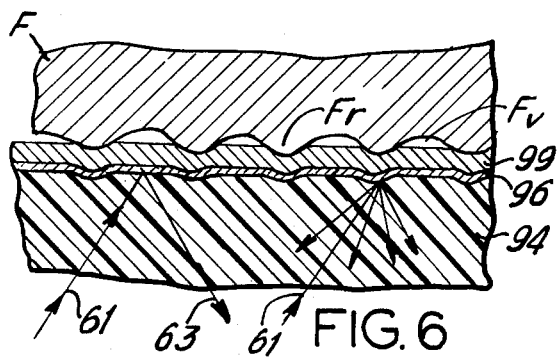
FIG. 6
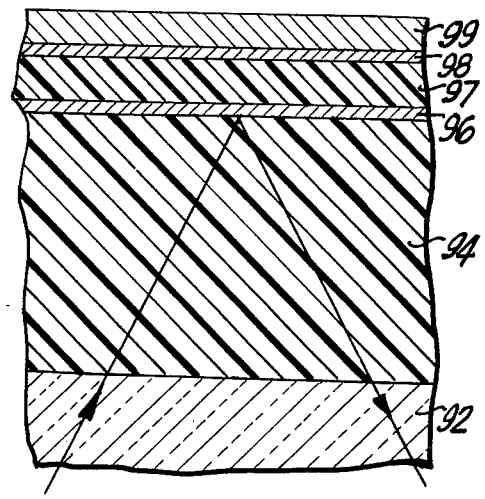
FIG. 7

FINGER IDENTIFICATION

REFERENCE TO RELATED APPLICATIONS

This application is a continuation-in-part of the following applications: co-pending application Ser. No. 210,174 entitled "Finger Identification" filed Nov. 25, 1980, now abandoned, which patent application is in turn a continuation-in-part of now abandoned patent applications (a) Ser. No. 042,605, entitled "Fingerprint Processing Method and Apparatus", filed May 25, 1979, which is a continuation-in-part of Ser. No. 844,719 having the same title and filed Oct. 25, 1977; and (b) Ser. No. 891,497 entitled "Finger Identification" filed Mar. 20, 1978, which is a continuation-in-part of Ser. No. 844,580 entitled "Fingerprint Processing Apparatus" filed Oct. 25, 1977. This application is also a continuation-in-part of co-pending application Ser. No. 396,813 entitled "Fingerprint Image Refinement" filed July 9, 1982, now abandoned.

BACKGROUND OF THE INVENTION

This invention relates generally to a finger identification and finger image processing apparatus. More particularly it relates to apparatus and method for encoding finger image information into machine readable signals with apparatus that is simple, inexpensive and reliable.

There are a number of systems that have been proposed for the processing of identification information based on the unique configuration of ridges and valleys in an individual's finger. When such information is taken from an ink impression of an individual's finger it is normally called a fingerprint. The more sophisticated techniques that employ optical techniques tend to provide a more refined, discriminate and accurate identification image; which image applicant has frequently called a fingerpress in order to distinguish it from the more primitive ink fingerprint. However, since both are based on the same unique ridge and valley finger characteristics, it should be understood that the term fingerprint is used by applicant generically. The term fingerprint object is used to refer to the actual configuration of the ridges and valleys of the finger when pressed against a surface. The term fingerprint image refers to the image of the fingerprint object that is obtained by using an optical system. In these optical systems, the finger of the subject individual is placed against the back of a transparent platen and the normally flat fingerprint object on the back surface of the platen is imaged through the front of the platen and projected as a fingerprint image onto receiving or processing equipment. This receiving equipment may take the form of a screen, a camera or an array of photocells.

For example, U.S. Pat. No. 3,138,059 discloses such a system. As described in the '059 patent, the finger is pressed against a transparent platen and a light beam is projected against the platen. Light is reflected from the finger to a recorder in the form of a camera. U.S. Pat. No. 4,053,228, issued on Oct. 11, 1977 discloses a holographic identification system the disclosure of which is incorporated herein by reference. As described in the '228 patent, a collimated, coherent light beam is projected against the front surface of a transparent platen. The light is reflected from the back surface of the platen, against which surface the subject's finger is pressed. The reflected light beam is modulated with the finger image and is correlated against a hologram of the same fingerpress to provide indentification.

However, systems of this type suffer from a number of disadvantages, foremost among which is a high degree of inaccuracy. That is, mismatching can easily occur between the hologram and the image. Mismatching error is reduced by employing accurate alignment procedures but this solution increases the cost and complexity of the system. Aside from the question of alignment apparatus, such systems are extremely expensive as they require beam splitters, devices to change direction of the light beams, focusing lenses, devices to effect the necessary correlations, etc. Additionally, these systems are difficult to maintain and service because of the number of elements comprising the systems and the fact that even the slightest vibration can knock a lens or a mirror out of position.

Accordingly, it is a major purpose of this invention to provide a technique for processing a fingerprint or fingerprint object in a fashion that is simple and unambiguous, that avoids undue messiness, provides a high degree of reliability in operation and that can be implemented in equipment which is relatively trouble free and that requires a minimum of maintenance.

It is a further object of this system to provide an accurate and unambiguous fingerprint image which in turn is susceptible to being encoded into machine readable signals.

In the holographic systems, stringent requirements are placed on the platen. The surfaces of the platen must be completely flat to minimize inaccuracies introduced into the reflected light beam. In general, where a lot of light is lost and where the contrast between the ridges and valleys in the image is low, the platen must be an expensive precision unit.

In addition, build up of finger oil introduces inaccuracies into the system. Often, a latent image is fixed to the platen by the finger oil residue on the platen. The operator must maintain the platen clean by wiping it after each use. However, even if the platen is clean, these systems are sensitive to either too much or too little oil from the finger. Either case may produce erroneous results. Other problems occur when the platen is cold and a warm finger is placed against it. This fogs the platen. While a platen may be preheated to eliminate this problem, such a solution is impractical.

Accordingly, a further object of this invention is to provide a highly accurate and reliable finger identification and processing apparatus that includes a relatively inexpensive platen.

Another object of the invention is to provide a finger receiving platen, for such an apparatus, that is insensitive to the amount of oil on a finger.

A further object of the invention is to provide optical fingerprint processing apparatus with greatly enhanced optical contrast between the valley zones and the ridge zones of the finger image.

Another object of the invention is to provide an optical scanning system which minimizes optical distortion, requires a minimum of optical components, and can be used for scanning of a fingerprint object on a platen as well as the scanning of a fingerprint image on a card.

A further object of this invention is to provide a system which is adapted to be used for both verification and identification. Verification is required in access control. Identification is required in police work.

BRIEF DESCRIPTION

In brief, a light source provides a light beam which is shaped by lenses into an interrogating beam of light. This beam is collimated and scanned across a finger placed against a platen. A finger pressed against the back surface of the platen provides a fingerprint object that is constituted by a series of ridges and valleys. The beam is directed towards the front surface of the platen, at a slight angle to normal, and passes through the transparent substrate of the platen to be reflected from the fingerprint object as a modulated beam.

The platen may have a deformable resilient layer that conforms to the pattern of ridges and valleys and that enhances the modulation of the light beam.

The light beam is scanned across the finger by a linear displacement scanning technique that maintains the angular relationship between the interrogating light beam and the plane of the platen throughout the scan.

At any position of the scan, the light beam is modulated by the object being scanned to produce light and dark spots corresponding to finger valley and ridge zones. This reflected modulated signal is projected on a linear array of photo-responsive devices; 512 charge coupled devices (CCDs) being employed in one embodiment. An imaging lens between the platen and the CCD array projects an image of the fingerprint. The CCD array is located at a plane in space that, depending on the choice of platen, is either at or displaced from the focal plane of the lens. The signals generated by the CCD array are serially interrogated to provide a digital output to represent the fingerprint information. An encoder is coupled to this scanning circuit and to the circuit that interrogates the array to make sure that the modulated beam of light is interrogated at regular predetermined intervals during the scan across the finger involved. In various embodiments, between 256 and 1024 such intervals are employed. By providing a mechanical optical scan in one direction and an electronic scan (of the CCDs) in the orthogonal direction, a simple implementation is provided to obtain a two dimensional scan with only a one dimensional displacement motion.

One of the platens employed is composed of multiple layers. The thickest layer is a glass substrate one surface of which forms the front surface of the platen. On top of the glass substrate is a deformable, resilient epoxy layer that provides a flat back surface. On top of the epoxy layer, a thin (3,000 Å thick) reflective silver layer is deposited. The silver layer is flat because it is deposited on the flat surface of the epoxy. The silver layer provides a mirrored surface to reflect the incident collimated light beam. The fourth layer is a fairly thin (for example, 0.05 mm. thick) layer of the same epoxy material. The subject's finger is applied to the back surface. When so applied, the epoxy deforms sufficiently to conform to at least the ridges. The result is a topographic map of the ridge and valley structure at the reflective silver surface. The ridges scatter the reflected light substantially more than do the valleys. This differential scatter provides a modulated reflected light beam. The use of the reflective layer provides a greater light intensity than when the reflective layer is omitted. In this multi-layer sandwich, the touching surface is isolated from the optically active surface and shields the optically active surface from the effects of temperature changes. These various layers also smooth or filter the ridge breaks in the input finger to provide a more usable and useful topographic map of the finger in the optically active silver layer surface.

Another embodiment disclosed herein employs a glass platen with a di-electric, anti-reflective coating on its back surface. A further embodiment employs a fingerprint card instead of the platen. There is also disclosed the use of an element to partially diffuse the collimated interrogating light beam to eliminate certain fine details and perform some of the filtering otherwise provided by the multiple layer resilient platen.

BRIEF DESCRIPTION OF THE DRAWINGS

FIG. 1 is an optical and mechanical schematic drawing of a first embodiment of a fingerprint processing apparatus constructed according to the present invention.

FIG. 2 is a block diagram illustrating the arrangement for encoding the fingerprint information.

FIG. 3 is a schematic optical diagram of a second embodiment of the apparatus constructed according to the present invention.

FIG. 4 is a sectional view orthogonal to the plane of FIG. 3, to an enlarged scale, of the movable platen portion of the FIG. 3 apparatus.

FIGS. 5 and 5A are a detailed sectional view, in somewhat schematic format, of one platen that may be used in the FIG. 1 and FIG. 3 apparatus with a finger impressed thereon. FIG. 5A is a very much enlarged view of the indicated portion of FIG. 5. It should be understood that FIG. 5A is even more schematic than is FIG. 5 and only schematically represents what is believed to be the relation between platen and finger ridges and valleys.

FIG. 6 is a view comparable to that of FIG. 5A, illustrating a second embodiment of the platen that may be used in the FIG. 1 and FIG. 3 apparatus. The FIG. 6 platen incorporates a reflective layer 96.

FIG. 7 is a schematic cross sectional view of a third platen embodiment having five layers on top of a glass substrate.

FIG. 8 is a view comparable to that of FIGS. 5A and 6 illustrating a fourth platen having an anti-reflective coating that is a di-electric.

FIG. 9A illustrates a finger image without the diffuser. FIG. 9C illustrates the sme individual's finger image with the diffuser.

DESCRIPTION OF THE PREFERRED EMBODIMENTS

The various embodiments described below differ from one another in certain major respects. One distinction has to do with what it is that is moved to effect the light beam scan. A second distinction has to do with the type of platen employed to provide the fingerprint or fingerprint object that is interrogated. A third distinction has to do with whether a platen or a fingerprint card is being read.

Figure 9:
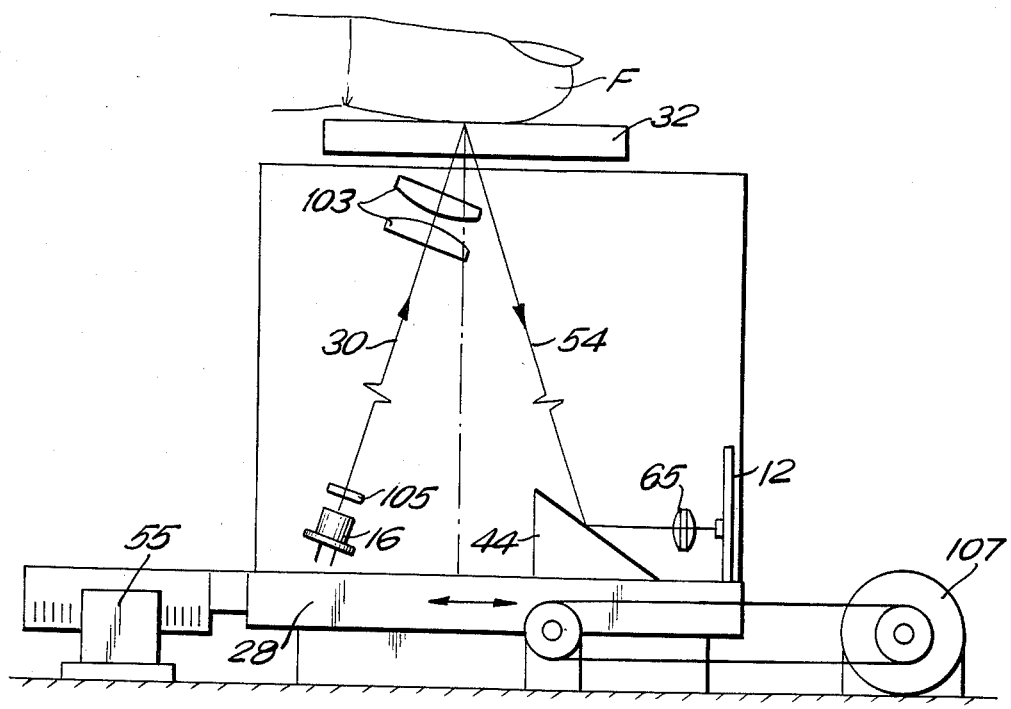
FIG. 9 is an optical and mechanical schematic showing a third and presently preferred embodiment of the apparatus adapted for use with an input finger on a platen.
Figure 10:
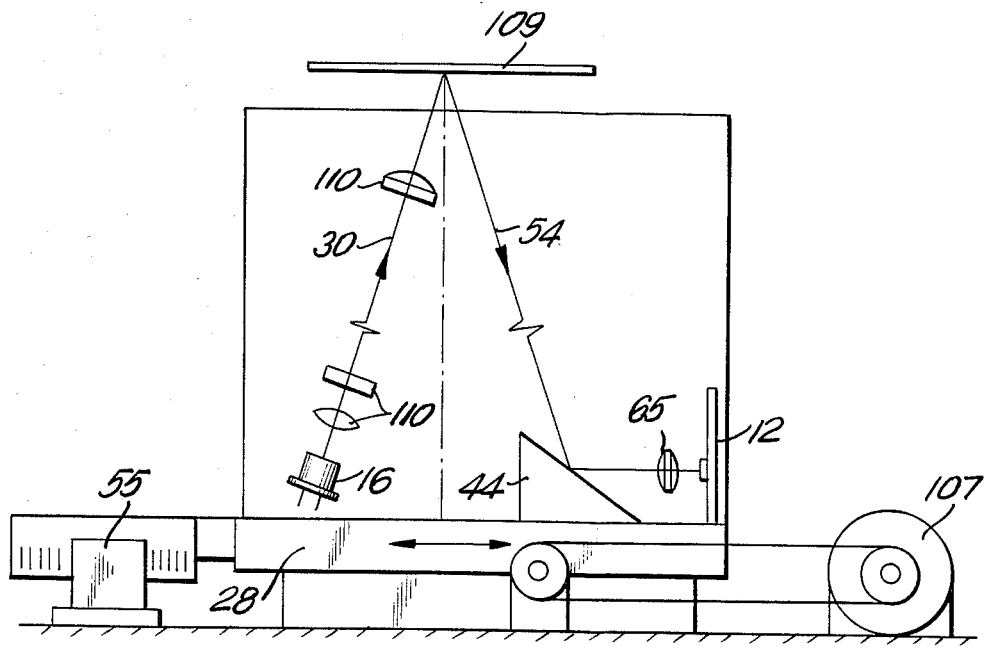
FIG. 10 is an optical and mechanical schematic of a presently preferred embodiment illustrating an application of the apparatus to reading or encoding of an input fingerprint card.

In the FIGS. 1, 9 and 10 embodiments, the interrogating light beam 30 is moved so that it scans across a stationary object. By contrast, in the FIG. 3 embodiment, a platen 64 and the finger F on the platen move across a stationary interrogating light beam 61, thereby effecting the scan.

The platen illustrated in FIG. 5 includes a deformable resilient layer 94. The platen of FIG. 6 includes a reflective layer 96 under the deformable, resilient layer. The platen of FIG. 7 includes a second deformable layer 97. The platen of FIG. 8 is a rigid glass platen with an anti-reflective di-electric layer 101.

The FIGS. 1, 3 and 9 embodiments are adapted for the reading or encoding of an input finger on a platen while the FIG. 10 embodiment is adapted for the reading or encoding of an input card having a fingerprint on the card.

The term collimate is used herein to refer to a light beam in which the light rays do not scatter. It is not essential that the light rays all be parallel to one another except at the focal point. It is only essential that they not cross over one another. Thus, a collimated light beam as used herein might be diverging, or parallel, or converging. In one embodiment of this invention the collimated light beam converges at an angle of a few degrees. Accordingly it should be understood that in the specification and claims, "collimate", or "collimation" is used as defined above. The laser 16 described provides a beam of coherent light. Coherent light is required in a holographic system. However, in the non-holographic embodiments described herein, the light beam does not have to be coherent. What is important is that the light beam be collimated in the broad sense of collimation as defined above. Accordingly, a point source has been found to be a useful light source. In one presently preferred embodiment the light source used is a high power solid state gallium arsenide infrared emitting diode, which is close to a point source. That light source provides a narrow frequency band of ±100 Angstroms. However, as is described in connection with the embodiment using the diffuser element 105, a small degree of diffusion or dispersion of the collimated light beam has been found desirable to filter very fine detail so as to provide a better image for electronic processing. Such partially diffused light is still substantially collimated. To put it another way, the collimation is still effective collimation except for very high spatial frequency features.

It should be understood in the following descriptions that the laser 16 is presently preferably replaced with a point source and the photodiode array is preferably a charge coupled device (CCD) array.

The FIG. 1 Embodiment

One embodiment of the apparatus constructed according to the present invention is designated generally by the reference numeral 10 in FIG. 1 and includes a linear photodiode array 12 mounted on a support 14. The array 12 is conventional in construction and may, for example, comprise photoresponsive array Model No. CCD 131 manufactured by the Fairchild Semiconductor Division of Fairchild Camera & Instrument Co., of Mountainview, Calif. This particular array comprises 1,024 photoresponsive elements that extend in the longitudinal direction (i.e., along a line going into the paper in the configuration of FIG. 1). The elements are aligned in contact with one another and each diode is about 0.02 mm. on a side. Accordingly, the shape of the light receiving opening of the array is in the form of a slit wherein the long dimension of the slit corresponds to the longitudinal direction of the array. Each element of the particular array 12 used is a charge coupled device (CCD).

The source of the light beam is a laser 16. The laser 16 normally produces a circular light beam of relatively small diameter in the order of approximately one millimeter. Cylindrical lenses 18 and 20 are positioned in the path of the light beam into a slit. As is conventional, the cylindrical lenses 18, 20 change the beam dimension along one axis and also collimate the beam along this axis. In an actual embodiment, the beam was stretched and collimated to about 20 mm. along one axis. The transverse axis of the beam remains one millimeter so that the shape of the interrogating beam 30 has a slit format roughly conforming to the format of the linear photodiode array 12.

To aid in visualization, the laser 16, the cylindrical lenses 18, 20 and the mirror 22 in FIG. 1 are rotated 90° to show the elongated light beam in the plane of FIG. 1. These elements must have an orientation that is rotated 90° from that shown to be consistent with the orientation of the rest of the apparatus as shown in FIG. 1. In FIG. 1, the interrogating light beam 30, the reflected modulated light beam 54 and the diode array 12 all have their long dimension perpendicular to the plane of FIG. 1.

Although a laser beam is shown, the light source need not be a laser nor even a source of coherent light. It is important however that the interrogating light beam 30 be collimated to maximize the differential scatter in the reflected light beam 54.

The modulated light beam 54 carries relatively light zones and relatively dark zones representing the ridges and valleys of the finger. By forming the light beam into a slit and then using that slit light beam to scan across the fingerprint, the level of light intensity available is much greater than in the arrangement shown, for example, in the U.S. Pat. No. 4,053,228 wherein the laser light beam is expanded so that it covers the entire area of interest of the finger involved. Shaping the light beam into the slit and scanning of the fingerprint with that slit light beam provides increased intensity of light at the array 12 to provide a signal level from the array 12 which facilitates a rapid electronic interrogation at each predetermined increment of the optical scan. This beam shaping has not been found necessary when using the infrared emitting diode mentioned above.

The mirror 22 reflects the shaped light beam as beam 24 toward mirror 26. The mirror 26, affixed to a movable support 28, reflects the light beam 24 as beam 30 to platen 32. The platen 32 receives a finger F thereon in contact with the upper surface of the platen.

The support 28 is movably mounted for reciprocating movement on arms 34 positioned at each end of the support and slidingly received in bores 35. The arms are supported by posts 37 upstanding from the support 14. Mounted on the top surface 36 fo the support is a member 38 having side walls 40 and 42 which terminate in shelves 41. In one embodiment, the sidewalls 40 and 42 form an angle of 42.5° with respect to the horizontal, for reasons noted in greater detail hereinbelow. The mirror 26 is affixed to the wall 40 and a mirror 44 is affixed to the wall 42.

A spring 46 between the support 28 and a wall 48 biases the support 28 toward the right, as shown in FIG. 1. An idler roller 50 is rotatably mounted adjacent the right-hand end of the support 28, as shown in FIG. 1. A motor drive cam 52 is drivingly connected with the idler wheel 50. The cam is shaped so that upon rotation of the cam by the motor the support 28 is driven to the left. As the cam rotates to the position shown in FIG. 1, the spring 46 returns the support 28 to its right-hand position.

The mirror 44 is in the path of a reflected modulated beam 54 from the platen 32 and reflects the light beam 54 to the CCD array 12. The beam 54, 56 is modulated with fingerprint information from the platen 32 as noted in detail below.

The angle of the mirror 26 causes the interrogating light beam 30 to strike the platen 32 at an angle 5° off normal. that is, the angle of incidence of the beam 30 with respect to a line perpendicular to the platen 32 is 5°. Similarly, the angle that the reflected beam 54 makes with the normal is also 5°. This insures that the reflected beam 54 will diverge from the interrogating beam 30.

The fingerprint information is modulated onto the slit light beam 30 when the finger F is pressed against the platen 32. The mode of modulation contemplated involves differential scattering of the light incident at the valley zones and ridge zones. Where the platen used has an anti-reflective coating on the back surface thereof this mode of modulation may also incorporate differential absorption and reflection from the ridge and valley zones. This differential scattering mode of modulation is explained in connection with the discussion of the platen structures shown in FIGS. 5, 6, 7 and 8.

More specifically, when a finger F is pressed against the back surface of the platen 32, a fingerprint object is created. That portion of the incident light which is reflected from the fingerprint object is modulated by the ridges and valleys of the finger to provide a reflected light beam 54 that carries the fingerprint information. A lens 65 serves to project an image of the fingerprint object to an image plane downstream. Depending on the platen used, the array 12 may be at the image plane or displaced from the image plane. The modulated slit light beam 56 striking the array 12 will contain light and dark spots which are indicative of the fingerprint information. This information is unique for each fingerprint and therefore provides encoded fingerprint information which can be retrieved or otherwise processed.

The incident light beam 30 is scanned across the finger (from right to left as taken in FIG. 1). The light beam 54 information is synchronized with the output from the diode array 12 by an encoder 55 which produces synchronizing signals that are applied to scanning circuitry by lead 57. The encoder 55 is conventional and produces a signal each time the support 28 moves an incremental distance. In one array 12 each of the diodes are about 0.02 mm. (about one mil) on a side. The encoder 54 produces a synchronizing signal each time the support moves 0.02 mm. While any type of encoder may be utilized, in practice an optical linear encoder has been used to generate synchronizing signals.

In operation, the finger to be examined is placed on the back surface of the platen 32. The laser 16 is energized to produce a slit light beam 30 that impinges on the finger pressed against the back surface of the platen 32. This light is modulated and reflected as light beam 54, 56 to the array 12. The encoder 55 produces a synchronizing signal which is applied to scanning circuit 58 (FIG. 2) via the lead 57. The scanning circuit 58 is conventional in construction and serially interrogates each element of the CCD array 12 in response to the synchronizing signal. The output of the scanning circuit 58, comprises a train of pulses for each scan line and is connected to the store or computer via a lead 60 so that the fingerprint information can be processed.

The cam 52 is energized with the laser 16 so that as the cam 52 rotates, the support 28 moves toward the left as taken in FIG. 1.

As the support 28 moves 0.02 mm towards the left, the light beam 30 similarly moves 0.02 mm and the modulation of the reflected light beam 54 changes in accordance with the ridges and valleys of the finger. The encoder 54 again produces a synchronizing signal which causes the scanning circuit 58 to again interrogate each one of the CCD elements comprising the array 12 to produce a second train of pulses representative of the fingerprint information in the second scan line.

This operation continues until the entire fingerprint object has been scanned by the light beam 30. The interrogation of the array 12 is accomplished electronically at a rate much faster than the rate of movement of the support 28 so that all CCD elements will have been interrogated before the light beam 30 is indexed to the next scan line.

One advantage of the scanning structure shown in that it is a linear displacement scanner. Thus displacement along a straight line of the mechanism, including the mirrors 26 and 44, causes the interrogating light beam 30 to be displaced without changing the angular relationship between the interrogating beam 30 and the fingerprint object being scanned and thus without changing the angular relationship between the reflected modulated light beam 54 and the fingerprint object being scanned.

The encoder 55 employed for the electronic scan is a position device. That is, it signals or requires an electronic scan at each predetermined incremental advancement of the optical scan. Accordingly, the system can tolerate small pertubations in the velocity of the optical scan. Thus there is no need to provide a highly sensitive and expensive constant velocity optical scan as long as the optical scan has a constant angle. By using position to guage the timing of the electronic scan a more stable result is achieved.

The FIG. 3 Embodiment

FIGS. 3 and 4 illustrate an arrangement in which the finger F is moved relative to the interrogating light beam 61 to effect the mechanical scanning operation. This is by contrast with the FIG. 1 embodiment where the interrogating light beam 30 is moved relative to the finger F. However both embodiments employ the basic concept of (a) a linear constant angle displacement scan between an interrogating light beam and a platen and (b) a synchronized electronic scan of a linear photoresponsive array 12 to provide an electronic scan orthogonal to the optical scan.

The arrangement shown in FIG. 3 includes a fixed support 62 on which the optical platen 32 is movably mounted. The support 62 has a central channel opening 66 through which the interrogating light beam 61 passes to impinge on the platen 32 and the reflected modulated light beam 63 passes to be further processed. The platen 32 is on a carriage 68 that rides on the upper surface of the support 62 by means of roller bearings 70. Affixed to the carriage 68 is an encoder 71 similar in construction to the encoder 54. Additionally, the carriage 68 is maintained in place by tracks 72 on the support 62 which are received in appropriate recesses in the underside of the carriage.

As shown in FIG. 3, the upper surface of the support 62 has a recess 74, the length of which is substantially longer than the carraige 68. A rod 76 extends between one end of the recess 74 and the carriage 68 and is adapted to be slidingly received in an opening 78 within the carraige. A speed reducing device 80 is connected to the carriage 68 and receives the rod 76 therethrough and is adapted to increase the coefficient of friction between the rod and the carriage to limit the speed of forward movement of the carriage 68 within the recess 74. For example, the device 80 may comprise a plurality of felt washers that receive the rod therethrough in a tight frictional fit.

In operation, the finger F is placed on the platen 32 with the tip of the finger in abutment with the end stop 82 of the carriage. The slit beam 61 from the laser is positioned so that it will impinge at the forward end of the finger when the elements are in the position shown in FIG. 3. The encoder 71 produces a synchronizing signal that causes the array 12 to be interrogated. Thereafter, the finger F exerts a continuous pressure in the forward direction thereby causing the carriage 68 to move toward the right, as taken in FIG. 3. As the carriage moves, its speed is limited by the device 80. Thus, as the finger moves relative to the light beam, the entire fingerprint or finger image is scanned in the manner noted above. The speed limiting device 80 prevents generation of a synchronizing signal while the array is still being interrogated from the preceding scan.

The Platen-In General

The linear displacement scanning technique of this invention has been described in connection with two embodiments without specifying the detailed nature of the platen 32 employed. A number of different platen devices have been developed to provide an improved and more usable image than hitherto has been available. Four different platen arrangements are described in connection with FIGS. 5, 6, 7 and 8 respectively. An essential part of the functioning of all four of these platens is that they provide a means whereby the degree to which the reflected light is scattered from under the ridge zones significantly differs from the degree to which reflected light is scattered from under the valley zones. This differential scattering results in differential processing of the reflected beam by the imaging lens 65 to provide differential intensity, at the array 12, representing ridge and valley zones.

Imaging lens 65 is a simple lens. Its ability to focus a reflected light ray as part of the fingerprint image downstream from the lens 65 depends upon the angle at which the reflected light ray is incident on the imaging lens 65. Reflected light which remains collimated is received by the lens at an angel essentially normal to the plane of the lens. Such light, and any reflected light within a few degrees off normal to the plane of the lens, will be focused not only at the image plane but also at substantial distances upstream and downstream from the image plane.

As the angle of the reflected light that is incident on the lens 65 deviates further from normal to the plane of the lens, the lens 65 will for a number of additional degrees be able to refocus that light as part of the image at the image plane. However such light will be rapidly defocused above and below the image plane.

Reflected light which is substantially scattered so that it is incident to the lens 65 at angles that deviate substantially from normal will not be refocused at the image plane or at any other plane upstream or downstream from the imaging lens.

The term "angular pass band" will be used herein in connection with the lens 65 to refer to that angular range within which the lens 65 will substantially refocus incident light at the image plane. Light that is scattered outside the angular pass band will simply be lost to the system in that the lens 65 will not be able to use such light to provide an image of that portion of the finger object which has so scattered the light. It should be understood that within the angular pass band significant collimation is lost for light rays which are scattered at the greater angles within the angular pass band and that collimation or substantial collimation is maintained only for light rays which are reflected at angles well within the center of the angular pass band.

Thus, depending on the relative differential scattering of the reflecterd light from under the ridge zones and the valley zones, the lens 65 will provide more or less focusing or defocusing of the two zones either at the image plane or removed from the image plane as is explained in greater detail in connection with the following description of each of the four different platens that have been developed and tested. What may be useful is to keep in mind that the basic notion behind all of the viable platen arrangements is the generation of differential scattering in the reflected light beam which is converted to differential intensity for detection and reading at the array 12 by the use of an imaging lens 65.

The FIG. 5 Platen

The FIG. 5 platen 84 has two layers. The two layers are a five millimeter (mm) thick transparent glass substrate 92 and a 0.25 millimeter thick, transparent, resilient, deformable epoxy layer 94. The readily deformable epoxy layer 94, deforms in response to the pressure of finger ridges $F_r$. The result is to provide a back surface for the platen 84 which provides a high degree of light scattering of whatever light is reflected under the ridge zones and a minimal amount of light scattering of whatever light is reflected under the valley zones $F_v$. As schematically shown in FIGS. 5 and 5A, when the collimated light beam 61 impinges on the relatively flat surface under the valley zone $F_v$, the interface between the epoxy layer 94 and the air under the valleys $F_v$ causes a small portion of the incident light 61 to be reflected, as part of the light beam 63, because of the difference in the index of refraction of the epoxy material 94 and air. Although only about 5% of the incident light is reflected under the valley zones $F_v$, this is sufficient to provide the valley images downstream at the photodiode array 12. Under the finger ridges $F_r$, the highly deformed areas in the highly compliant epoxy material 94 cause a much greater degree of light scatter in the reflected light. The reflected light scatters at angles substantially outside of the angular pass band of the simple imaging lens 65. As a consequence, at the image plane, the valley zones are recreated while the ridge zones are essentially dark.

The result is a clear-cut pattern, received at the array 12 as a slit having alternating light and dark spots. The spots corresponding to the finger valleys are relatively light while the spots corresponding to the ridges are essentially entirely dark.

The scattering depicted by the arrows in FIGS. 5, 5A and 6 is highly schematic. The arrows are not intended to suggest actual angles of scatter but only that the reflected light is scattered.

It is believed that there is some scattering of light under the valley zones $F_v$, but that this scattering is well within the angular pass band of the imaging lens 65 so that substantially all of the reflected light at the valley zone is reflected as collimated light and can be detected by the array 12 at the image plane and at positions displaced from the image plane.

In addition, because of the fact that most fingers carry substantial amounts of finger oil which has an index of refraction very similar to that of the epoxy material 94, there will be substantial absorption of the incident light 61 at the ridge zones $F_r$. Thus, in the FIG. 5 platen, the absorption of light due to index of refraction match will complement the effect of the scattering of light under the ridge zones. However, one advantage of the FIG. 5 platen is that even with a very dry finger, in which there is little or no light absorption at the ridge zones, the substantial scattering of light results in an image downstream that has sufficient differential intensity between the ridge zones and valley zones to provide a usable input for the detecting array 12.

In order for the FIG. 5 platen to operate effectively, it is important that the index of refraction of the epoxy layer 94, or other readily deformable resilient material, be as close as possible to that of the glass 92 or other transparent substrate material that may be used. Matching the index of refraction of the layers 92 and 94 will minimize the amount of light lost by reflection from the interface between the layers 92 and 94. In one embodiment, a transparent optical epoxy is used which is manufactured by Epoxy Technology Inc., 65 Grove Street, Watertown, Mass. 02172 and is designated by the Model No. EPO-TEK No. 305. The index of refraction of this epoxy is 1.511. The epoxy used should be specified as one which when cured will readily deform when pressure in the range of 5 kilograms per square centimeter (about 2 p.s.i.) is applied.

It is also important that the epoxy material 94 be resilient as well as readily deformable so that essentially no latent image will remain in the epoxy once the finger F has been removed.

Furthermore, because the FIG. 5 platen 84 generates finger information by a different physical effect than by optical matching or mis-matching by finger oil causing different reflectivity, the problem of finger oil deposition is of little concern. This eliminates the need to continuously clean the working surface of the platen 84. Accordingly, the cost of the platen 84 as compared with platens previously used is minimal and the cost of operating with the platen 84 is also minimized.

The array 12 is preferably at the image plane. But if it is displaced from the image plane by a small amount it will receive an image. Light spots representing the valleys will appear with an intensity that is a function of a scale factor due to light beam divergence or convergence and that may be affected by a small degree of light scatter that occurs at the valley zones.

The FIG. 6 Platen

The platen of FIG. 6 has four layers. One of the four layers is the five mm. thick transparent glass substrate 92 shown in FIG. 5. The other layers are the 0.25 mm. thick transparent, resilient, compressible epoxy layer 94, a three thousand/Angstrom (3,000 Å) thick reflective silver layer 96 and a 0.025 mm. thick protective lacquer layer 99. The lacquer layer 99 is the surface layer against which the subject's finger F is pressed. The lacquer layer 99 is quite compliant and the pressure of the finger ridges $F_r$ is transmitted through to the silver layer 96 and epoxy layer 94. From the point of view of the reflected light, it is the reflective silver layer 96 which can be considered as the back surface of the platen. The readily deformable epoxy layer 94 deforms in response to the pressure of the finger ridges $F_r$. The combined operation of the deformable layer 94 and the reflective layer 96 is to provide enhanced contrast between the ridges $F_r$ and the valley $F_v$ of the image of the finger that is reflected downstream from the finger F.

As schematically shown in FIG. 6, when the interrogating light beam 61 impinges on the flat surface of the silver reflective layer 96, it bounces off with an angle of reflection that is equal to the angle of incidence. Thus the light beam portions 63 reflected from the flat surface portions of the silver surface 96 will remain collimated. However, these flat portions of the silver surface 96 are only the portions under the valleys $F_v$ of the applied finger F. As also schematically shown in FIG. 6, under the ridges $F_r$ of the applied finger F, the silver surface 96 is deformed in response to deformation of the deformable, resilient epoxy 94. The rounded reflective surface under these ridges $F_r$ will cause the incident light beam 61 to scatter.

Thus the operation of the FIG. 6 embodiment is similar to that of the FIG. 5 embodiment. One major difference is that in the FIG. 6 platen, the reflective layer 96 assures that the level of light intensity downstream will be very much greater than that provided by the FIG. 5 platen. In particular, the pattern received at the array 12 will have a light intensity determined by the fact that 100% of the incident light is reflected from the FIG. 6 platen as contrasted with the approximately 5% of light reflected in the FIG. 5 platen. A second difference is that because of the moderating effect of the lacquer layer 99, the amount of deformation due to the ridges $F_r$ at the reflective layer 96 is somewhat less than the amount of deformation in the FIG. 5 platen. Accordingly, in the FIG. 6 embodiment, the degree of scatter under the ridges is not quite as great as the degree of scatter under the ridges of the FIG. 5 embodiment. This may be one of the reasons why, in the FIG. 6 embodiment, the array 12 cannot, as a practical matter, be placed at the image plane of the lens 65. The image at the image plane is a fairly uniform bright plane in which whatever distinction there may be between the valleys and ridges cannot be particularly noticed or detected by the array 12. In large part, this is because much of the light scatter under the ridges in the FIG. 6 platen is sufficiently within the angular pass band of the lens 65 so that the reflected light is essentially imaged at the image plane. However one or two millimeters from the image plane, the scattered light from the rounded areas under the ridges is not properly focused thereby providing a contrast between ridge and valley zones.

What happens is actually not entirely understood by applicant at present. Downstream from the image plane, the defocused ridges appear dark while the substantially collimated light from the valley zones remains quite bright. The contrast between the dark spots and the light spots representing ridges and valleys respectively is a substantial contrast and certainly very much greater than the magnitude of any contrast available from the FIG. 5 platen. Upstream a millimeter or two from the image plane, the valleys, as expected, remain substantially as bright as at the image plane, However, somewhat surprisingly, the ridges achieve a light intensity substantially brighter than that of the valleys.

A flat reflective layer 96 can be achieved when applying and bonding the epoxy layer 94 to the glass substrate 92. When so applying the epoxy, a highly precise, highly flat master can be employed as the means for determining the epoxy surface. In practive, silver is vacuum deposited on a highly flat master glass element. The epoxy (10 to 15 mg.) in liquid form is placed on top of the silver and then the glass substrate 92 is placed on top of the epoxy and held in position 0.23 to 0.25 mm. spaced from the master. When the epoxy is cured, the silver layer 96 lifts off the master glass together with the epoxy layer 94 and glass substrate 92. Lacquer is then sprayed on the silver to provide the layer 99.

The reflective surface 96 of the FIG. 6 platen is held to a high degree of flatness in order to minimize interfering background noice.

Because the reflective layer blocks light from behind it, finger oil has no effect on the operation of the platen and thus noise due to a latent image or other interference is eliminated.

The FIG. 7 Platen

The FIG. 7 platen is the presently preferred platen. It incorporates two layers in addition to those described in connection with the FIG. 6 platen. These two layers are a second deformable resilient epoxy layer 97 and a second silver layer 98. The silver layer 96 is still the optically active reflective surface.

The layers 94, 96, 97 and 98 in combination form a sandwich which isolates the optically active surface at the layer 96 from the touching surface at the layer 99. This shields the optically active surface, specifically the silver layer 96, from the effects of minute shrinking or expansion caused by temperature changes. Essentially, because the optically active reflective layer 96 is in suspension between two of the same materials, the epoxy of layers 94 and 97, it exhibits no external surface effects.

The lacquer layer 99 conforms very readily to the incident finger and provides the durability required to protect the layers beneath it.

A very important factor is that the layers 97, 98 and 99 together perform an important function of smoothing of filtering ridge breaks in the input finger. Thus the topographic map formed on the optically active surface of the layer 96 will be a mechanically filtered, and thus a somewhat idealized, version of the actual finger image. This elimination of certain discontinuities provides for a much simpler signal processing, feature extraction and matching in the downstream electronics.

Fabrication of the FIG. 7 platen is preferably one in which the epoxy layer 94 and the silver layer 96 are initially fabricated against an ultra precise flat master. The silver layer 96 is the release agent for the epoxy layer 94. The silver is initially deposited on this master and is removed with the epoxy layer 94 when the epoxy layer 94 is molded against the master. After the layers 94 and 96 are cured, the layers 97 and 98 are molded again against a precise master with the silver layer 98 acting as a release agent. This second silver layer 98 would not be required except for its function as a release agent in the molding of the second epoxy layer 97. The lacquer layer 99, being very compliant, does not require being placed on with extreme flatness. The epoxy layer is useful not only for its durability in protecting the other layers but also because it operates as part of the mechanical filtering function mentioned above.

In one embodiment, the thickness dimensions of the layers in the FIG. 7 platen are a glass substrate 92 that is nominally 6 mm. thick, a first epoxy layer 94 which is 0.25 mm. thick, a second epoxy layer 97 which is 0.050 mm. thick and a lacquer layer 99 which is 0.025 mm. thick. The two silver layers 96 and 98 are approximately 3,000 Angstroms thick.

The FIG. 7 platen operates very much as does the FIG. 6 platen and the discussion of the FIG. 6 platen applies to the FIG. 7 platen. The FIG. 7 platen is preferred over the FIG. 6 platen primarily because of the improved filtering and better shielding of the reflective layer 96.

The displacement of the array 12 from the image plane is only a relatively slight displacement. In one embodiment employing the FIG. 7 platen, the array 12 has an optimum and preferred position upstream from the image plane. The array 12 position is a function of the quality of the finger image or fingerprint being interrogated. In that embodiment, where a good fingerprint is provided in which the distinctions between the ridges and valleys are quite clear cut, the optimum position of the array 24 is between 0.5 mm. and 0.7 mm. upstream from the image plane where the imaging lens 65 has a 20 mm. focal length. For degraded fingerprints, the optimum position of the array 12 is 2.5 mm. upstream from the image plane. A preferred embodiment of the invention incorporates a mechanism for permitting operator selection of the lesser or greater distance from the image plane by providing two different lenses 65 having slightly different focal lengths. The two lenses 65 are mounted on a movable mount that permits the operator to selectively position one or the other of the two lenses 65 in the path of the modulated reflected light beam 63.

The light intensity at the array 12 upstream from the image plane is three to five times greater at the ridge zones than at the valley zones. It is believed that this observed brilliant intensification which occurs slightly upstream from the image plane comes about because of the combined effects of the non-planarity of the object being imaged and the smooth continuous ridge contours provided by the mechanical filtering due to the layers above the reflective layer 96.

It is presently preferred to deploy the array 12 slightly upstream from the image plane rather than slightly downstream from the image plane because of the noise problem in the relatively dark areas representing the ridge zones downstream. The relatively constant valley zone illumination due to the essentially collimated light provides a minimum noise problem in the valley zones either upstream or downstream from the image plane. However, the distinctive intensification of intensity representing ridge zones upstream of the image plane contrasts with the somewhat noisy relatively dark zones representing the ridges downstream.

It has been observed that the substantial light intensification representing the ridge zones upstream is coupled with a decrease in the width of the ridge zones image. Thus what is observed is a sharp bright line representing the ridge zones at the array 12. The electric field reinforcement which provides this substantially greater intensity at the ridge zones occurs where the collimated light is also coherent. However, where incoherent collimated light is employed as the interrogating light beam 61, the light intensification is also observed. However the extent of the intensification is somewhat less than when coherent light is employed and the significantly distinctive narrowing of the ridge image zones does not occur.

Although some mechanical filtering does occur in connection with the FIG. 6 design, the significant and dramatic improvement in the providing of a stylized image that can be readily processed in provided by the entire multi-layer arrangement shown in FIG. 7. In particular, the second epoxy layer 97 appears to be the element which is the most significant to provide the improved filtering effect.

In one embodiment of this invention, the apparatus employs the FIG. 1 system with the FIG. 7 platen. The platen is stationary and the interrogating beam moves across the finger. That embodiment incorporates the following dimensional relationships. The approximately 1 mm. laser beam is shaped by the lenses 18 and 20 to form a slit beam that is 15 mm. long at the second cylindrical lens 20. the two lenses 18 and 20 are positioned so that their focal points are not coincident. The front focal point of the lens 18 and back focal point of the lens 20 are slightly spaced from one another so that the slit beam converges slightly as it travels downstream from the second cylindrical lens 20. This convergence is only a few degrees so that the slit beam 30 at the platen 23 has a length of about 12 mm. The imaging lens 65 has a 20 mm. focal length and is about 110 mm. downstream from the finger object. The converging slit beam is focused at an image plane which is about 24 mm. downstream from the lens. The photodiode array 12 plane is one millimeter upstream from the image plane and receives the modulated slit light beam having a length of about 2.3 mm. In that embodiment an array of 256 photocells is employed which has a length of about 3.3 millimeters so that not all of the cells are employed. For degraded fingers, the 20 mm. lens is replaced with one having a 25 mm. focal length. In that case, the distance from the finger object to the lens 65 is about 115 mm., the image plane is 32 mm. from the lens 65 and the array 12 is 4 mm. upstream from the image plane.

The FIG. 8 Platen

A fourth platen 100 which has been tried with success is illustrated in FIG. 8. In this platen, the glass substrate 92 has, on its back surface, an anti-reflective coating 101. The platen has no other layers. This anti-reflective coating 101 is termed such because it reduces the magnitude of reflection at the interface between air and the back surface of the platen 100. As a consequence, at the interface, all of the incident light, at least ideally, passes through the back surface of the platen and, as shown in FIG. 8, is incident against the valleys of any finger F applied thereon. This coating further calls for the magnitude of reflection at the discontinuity with a further layer of glass (or with a further layer of any substance, such as finger oil, having substantially the index or refraction of glass) to be substantially greater than the magnitude of reflection at the discontinuity between glass and air. The important thing is to have as great a difference between the two magnitudes of reflection as possible, with the reflection at the discontinuity with air being relatively minimal and the reflection at the discontinuity with finger oil being relatively maximal.

With such a platen, it is possible to obtain a usable image at the image plane downstream from the lens 65 regardless of how oily or dry is the finger F. What happens is that if there is appreciable finger oil, then the reflection of the incident light at the ridges is maximum. In one embodiment, about 10% of the incident light is reflected. At the valley zones, essentially no light is reflected from the interface between platen and air. The light reflected from the valleys is so highly scattered that it falls outside of the angular pass band of the lens 65 and thus is not focused.

However, where the finger is extremely dry, there will be a refraction index mismatch under the ridges. But, the ridges themselves reflect the incident light. Because the ridges are pressed against the back surface of the FIG. 8 platen, they are sufficiently flat so that the degree of scatter of the reflected light is within the angular pass band of the lens 65. Thus an image will be formed at the image plane although the brightness of the zones representing the image will be less than when an oily finger is applied to the platen. In this fashion, by use of an anti-reflectant coating 101, the range of fingers which can be processed by the system of this invention is greatly extended because the finger oil is not a prerequisite for the system to interrogate the finger being presented.

Because there is scattering of the reflected light from the ridge zones when a dry finger is applied, there is a great deal of defocusing of the ridge zone light at positions off the image plane. Accordingly, when using a FIG. 8 platen, it is important that the detection array 12 be positioned essentaily at the image plane.

FIG. 8 represents a scattering under the ridges although the degree of scatter, like the degree of scatter under the ridges in FIG. 6, is within the angular pass band of the lens 65. By contrast the degree of scatter under the valleys in FIG. 8, like the scatter under the ridges of FIG. 5A, is substantially outside the angular pass band of the lens 65.

One problem with the FIG. 8 type of platen is that the finger oil left by an applied finger may run leaving a film which will tend to interfere with the next subsequent applied fingerprint. This problem is substantially eliminated by use of a di-electric (electrically non-conductive) anti-reflective coating 101. Because the coating 101 is selected to be di-electric, any charge that builds up between the finger applied and the platen tends to pull off the finger oil when the finger is removed.

A product designated as No. 7028 from Metavac, Inc. of 44–68 162nd Street, Flushing, N.Y. 11358 is a useful anti-reflectant coating with adquate di-electric properties. When used as the coating 101, it provides a reflection of substantially under 1% of the incident light at a discontinuity with air; that is, under the valley zones, and a reflection of about 10% at discontinuity with finger oil; that is, under the ridge zones. With this coating, where a dry finger is applied, the amount of reflected light at the ridges may drop to as little as 5% of the incident interrogating light but that has been found adequate to provide a distinctive image at the image plane.

In general, most light sources, whether coherent or incoherent, tend to have a frequency range within which the light is concentrated. The frequency range generally has to be specified as part of the specification for the anti-reflectant coating. The particular Metavac product No. 7028 is employed with a light source having a frequency in a narrow band of perhaps 200 Å centered on 6,328 Å in one case and 8,200 Å in another case. The coating 101 must be tuned to the frequency of the light source.

The Platens Compared

An analysis of how the system of this invention operates with the different types of platen arrangements shown requires, in general, consideration of the effects of (a) the extent to which the ridge zones cause scattering of reflected light and (b) the extent to which the finger oil from the ridge zones affects optical matching or mismatching to absorb or reflect indicent light.

Where the reflective layer 96, such as is shown in FIGS. 6 and 7 is employed, the finger oil has no effect. That is one of the advantages of those embodiments.

Other embodiments can be selected so that the scattering cooperates with the oil matching or mismatching effect to provide an enhanced result. Thus in the FIG. 5 embodiment, the optical matching between whatever oil is on the finger and the epoxy layer 94 results in a reduction of reflected light in the ridge zones. Whatever light is reflected is scattered to such a large degree that much of it is outside of the angular pass band of the lens 65 and thus is not reformed at the image plane. Accordingly in the FIG. 5 platen embodiment, light absorption due to the oil and light scattering due to the ridges are reinforcing effects to provide a dark ridge zone at the image plane. Where a very dry finger is involved, so that there is less than the usual amount of absorption due to optical match between oil and epoxy, the high degree of scattering under the ridges tends to assure a usable image in the image plane.

Similarly, in the embodiment shown in FIG. 8, where an oily finger is applied, the anti-reflectant coating 101 causes essentially collimated light reflection under the ridge zones and highly scattered reflection under the valley zones. Where a very dry finger is applied, the light reflected from the relatively flattened ridge zones is refocused to the image plane. Thus whether an oily finger is applied or a very dry finger is applied, there will be a usable and significant ridge zone image at the image plane. In this fashion, light reflection due to the oil and light reflection due to the ridges are reinforcing effects to provide a light ridge zone at the image plane. When contrasting the FIG. 8 platen with the FIG. 5 platen, it must be kept in mind that because of the flattening of the ridge zones the extent of the light scattering from the ridge zones in the FIG. 8 arrangement is substantially less that in the FIG. 5 arrangement so that most of the light scattered from the ridge zones in the FIG. 5 arrangement is outside of the angular pass band of the lens 65 and much of the light reflected from the ridge zones in the FIG. 8 arrangement is within the angular pass band of the lens 65.

The FIG. 9 Embodiment

FIG. 9 illustrates an embodiment developed subsequent to those shown in FIGS. 1 and 3 as a further preferred embodiment. Corresponding reference numbers are used where appropriate. Briefly, a light source 16 provides a collimated light beam which is shaped by condensing lenses 103 to interrogate the fingerprint object that is applied by the finger F on the back surface of the platen 32. Because of the availability of more intense light sources, it is not found necessary to provide a slit light beam design such as illustrated in connection with FIGS. 1 and 3. Accordingly, the condensing lenses 103 are not the cylindrical lenses 18, 20 shown in the other embodiments. The slide table 28 rides on a rail and is supported on ball bearings. The drive motor 107 drives the table. Solid state switches detect the end motion of the table 28 and serve to reverse the motor 107 so that the table 28 can be driven in both directions. A diffuser element 105 creates a partially diffused, substantially collimated interrogating light beam 30. This partially diffused interrogating light beam is useful to filter certain very fine structure and to prevent what appears to be an over modulation effect with certain fingers and thus extends the range of fingers on which the device of this invention can be used. This partially diffused, but still substantially collimated, beam also serves to filter out certain fine detail and reduces the amount of salt and pepper artifact in the image provided.

Otherwise the elements shown in the FIG. 9 embodiment such as the imaging lens 65, the photodetector array 12 and the linear encoder 55 perform the same functions as described in connection with FIGS. 1 and 3.

The diffuser element 105 is positioned in the interrogating light beam 30 and preferably is positioned immediately adjacent to the beam from the collimated light source 16. A standard ground glass element is used as the diffuser. The result is to create some crossover of the light rays within the interrogating beam 30. However, the diffusion is not so great as to cause complete diffusion and loss of directivity for the light within the light beam.

Figure 9A:
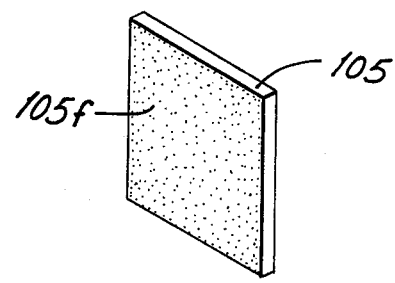
FIG. 9A is an enlarged illustration of a typical glass diffuser element having a ground surface used in the FIG. 9 embodiment.

The diffuser element 105 is a small glass plate having a ground surface 105f as indicated in FIG. 9A. In one embodiment that has been tested, the dispersion plate 105 has a grain size of ten micrometers in diameter. It is not believed that there is anything critical about the grain size on the ground glass surface 105f except too fine a grain size might create so much diffusion as to seriously degrade the collimation of the interrogating beam and too great a grain size would generate too little diffusion to create the results desired. Also, it is not believed that the material of the plate 105 is of any great significance.

In the absence of the diffuser element 105, the ridge image at the array 12 becomes distorted for certain individuals. For certain individuals who have a pronounced ridge to valley height in their finger, there is a degree of ridge image breakup and even some twinning of the ridge image at the array 12. This phenomenon limits the scope of utility of the apparatus. However, the addition of the diffuser element 105 obviates this problem without losing any of the population having a relatively smooth (that is low ridge to valley height) finger surface.

Figure 9B:
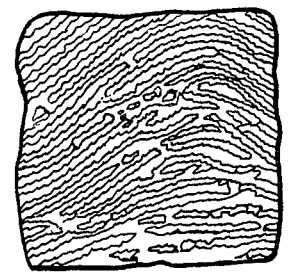
FIGS. 9B and 9C schematically illustrate and contrast the finger image obtained with and without the FIG. 9A diffuser element.
Figure 9C:
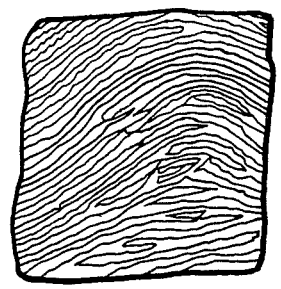

An example is illustrated schematically in FIGS. 9B and 9C, FIG. 9B shows the kind of broken up image that occurs in connection with certain individuals when the FIG. 9 system is employed without the diffuser element 105. FIG. 9C shows the improved result with the diffuser element 105. FIGS. 9B and 9C are taken from the same individual. The difference between the two figures can be noted with the eye. However, the effective difference between the two figures in terms of any automatic processing apparatus is far more significant than might appear to the eye. The unwanted breaks that are shown in FIG. 9B tend to confound any enrollment or identification apparatus because these breaks do not reflect legitimate minutia. One of the important consequences of this is that these breaks are not repeatable and the individual who is enrolled with the FIG. 9B input fingerprint will not reliably be identified at subsequent times. In order to get reliable and repeatable identification, it is important that only the classical minutia be identified and enrolled.

The diffuser element 105 can be profitably used with the hard glass platen 92 having the di-electric, anti-reflective coating 101 on the finger touching surface illustrated in FIG. 8. When the invention is employed in connection with such a hard glass, anti-reflective, di-electric coated platen, the position of the array 12 may have to be displaced very slightly (a few mils) from the image plane of the lens 65 in order for the diffuser 105 to have an optimum effect.

This diffuser 105 also provides a filtering of very fine structure without destroying the substantially collimated nature of the interrogating light beam. This effective filtering of fine structure is in large part done in a mechanical fashion by the resilient, deformable platens and thus the diffuser element is not as important to use with a FIG. 7 platen as it is with a FIG. 8 platen. It should be understood, however, that the resilient, deformable platens as well as the anti-reflectant coated hard glass platen may be used with the diffuser element 105.

The FIG. 10 Embodiment

The arrangement of this invention has been found useful for the interrogation of regular fingerprint input cards. This embodiment which is shown in FIG. 10 is similar to that of FIG. 9 except that ab input card 109 is employed instead of the finger F and platen 32. Furthermore, because of the greater amount of light required to read the range of input cards which may be provided, it has been found preferable that the lens arrangement 110 provide a slit forming function as well as a condensing function. In addition, the diffuser 105 that has been found preferable in the FIG. 9 embodiment is not needed in the FIG. 10 embodiment because of the nature of the input image.

What is claimed is:

1. Fingerprint processing apparatus comprising:
a source of an interrogating light beam,
means to provide a fingerprint object having ridge zones and valley zones in the path of said interrogating light beam,
said object modulating said interrogating light beam to provide a reflected light beam modulated with fingerprint information,
linear displacement optical scanning means for causing said interrogating light beam to scan the fingerprint object and for maintaining the angular relationship between said interrogating beam and the fingerprint object being scanned constant throughout the optical scan,
an array of photoelectric transducers optically downstream from said platen, and
lens means positioned in said reflected light beam to provide a fingerprint image at said array,
said array being arranged in a predetermined linear form for receiving said modulated light beam and for converting the fingerprint information carried by said modulated light beam into a plurality of sets of information signals representing a line by line scan of the fingerprint object, and
electrical scanning means to electronically scan the information signal outputs of said array and to synchronize said electric scan to incremental positions of said linear displacement scanning means to provide a relatively faster electronic scan along said array and a relatively slower optical scan along an axis transverse to said array, said slower optical scan being effected by the linear displacement between the light beam and the fingerprint object.

2. The apparatus of claim 1 further comprising:
a platen in the path of said interrogating light beam and adapted to receive a finger thereon to provide a fingerprint object at a predetermined surface to cause differential scattering of said reflected light beam, the reflected light from zones corresponding to the finger ridges scattering substantially differently than the reflected light from zones corresponding to the valleys of said fingerprint object,
said fingerprint image at said array having differential light intensity representing valley and ridge zones, the difference in light intensity at said fingerprint image deriving substantially from said differential scattering of said reflected light from said fingerprint object.

3. The apparatus of claim 1 wherein:
said interrogating light beam is a partially diffused, substantially collimated light beam.

4. The apparatus of claim 2 wherein:
said interrogating light beam is a partially diffused, substantially collimated light beam.

5. The apparatus of claim 2 wherein:
said platen comprises a transparent substrate and a di-electric anti-reflective coating on the finger receiving surface thereof,
said reflected light from the zones corresponding to the ridges of said fingerprint object scatters substantially less than said reflected light from the zones corresponding to the valleys of said fingerprint object.

6. The apparatus of claim 1 wherein: the reflected light from one of said valley or ridge zones of said fingerprint object falls substantially within the optical aperture of said lens means and the reflected light from the other of said zones falls substantially outside of said optical aperture.

7. The apparatus of claim 2 wherein: the reflected light from one of said valley or ridge zones of said fingerprint object falls substantially within the optical aperture of said lens means and the reflected light from the other of said zones falls substantially outside of said optical aperture.

8. The apparatus of claim 5 wherein: the reflected light from said ridge zones of said fingerprint object falls substantially within the optical aperture of said lens and the reflected light from the valley zones of said fingerprint object falls substantially outside of said optical aperture.

9. Fingerprint processing apparatus comprising:
a source of a substantially collimated interrogating light beam,
a platen in the path of said interrogating light beam, said platen having a finger receiving surface to receive a finger there on to provide a fingerprint object having ridge zones and valley zones,
said finger receiving surface of said platen, when a finger is applied thereto, modulating said interrogating light beam by scattering the reflected light from said ridge zones substantially differently than the light reflected from said valley zones to provide a reflected light beam modulated with finger information, linear displacement optical scanning means for causing said interrogating light beam to scan said fingerprint object on said platen and for maintaining constant the angular relationship between said interrogating beam and said fingerprint object being scanned throughout the optical scan, an array of photoelectric transducers optically downstream from said platen, and a lens positioned in said reflected light beam to provide at said array a fingerprint image having differential light intensity representing valley and ridge zones respectively, said array being arranged in a predetermined linear form for receiving said modulated light beam and for converting the fingerprint information carried by said modulated light beam into a plurality of sets of information signals representing a line by line scan of the fingerprint, and electrical scanning means to electronically scan the information signal outputs of said array and to synchronize said electronic scan to incremental position of said linear displacement scanning means to provide a relatively faster electronic scan along said array and a relatively slower optical scan along an axis transverse to said array.

10. The apparatus of claim 9 wherein:
said platen comprises a transparent substrate and a di-electric anti-reflective coating on the finger receiving surface thereof.

11. The method of examining a fingerprint in which a finger is placed on a platen to provide a fingerprint object having ridge zones and valley zones comprising the steps of:

scanning a light beam across said object by moving said platen and said light beam relative to one another and causing the angular relationship between said interrogating light beam and said fingerprint object being scanned to remain constant throughout the optical scan, modulating said interrogating light beam with said fingerprint object to provide a reflected light beam modulated with fingerprint information, said step of modulating being effected by scattering the reflected light from the ridge zones substantially differently than the reflected light from the valley zones, imaging the reflected light by converting the differential scatter of the reflected light from the ridge and valley zones to differential intensity representing ridge and valley zones thus providing a fingerprint image, detecting said fingerprint image on a line by line basis to provide a set of electrical signals representing light intensity along each of said lines of said fingerprint image, and electronically scanning each of said detected lines, and providing a plurality of relatively faster electronic scans simultaneous with the relatively slower optical scan.

12. The method of claim 11 wherein said reflected light from the zones corresponding to the ridges of said fingerprint object scatters substantially less than does said reflected light from the zones corresponding to the valleys of said fingerprint object, and said step of detecting occurs substantially at the image plane of a lens used in said step of imaging.

13. The method of claim 11 wherein said reflected light from the zones corresponding to the ridges of said fingerprint object scatters substantially more than does said reflected light from the zones corresponding to the valleys of said fingerprint object, and said step of detecting occurs at a plane displaced from the image plane of a lens used in said step of imaging.

* * * * *